US00PP23166P2

(12) United States Plant Patent
Endisch

(10) Patent No.: US PP23,166 P2
(45) Date of Patent: Nov. 6, 2012

(54) ***MANDEVILLA* PLANT NAMED 'GENDIPBIC'**

(50) Latin Name: *Mandevilla sanderi*
Varietal Denomination: Gendipbic

(76) Inventor: Gerd Endisch, Hagenbach (DE)

( * ) Notice: Subject to any disclaimer, the term of this patent is extended or adjusted under 35 U.S.C. 154(b) by 0 days.

(21) Appl. No.: 13/065,421

(22) Filed: Mar. 22, 2011

(51) Int. Cl.
*A01H 5/00* (2006.01)

(52) U.S. Cl. ..... Plt./232

(58) Field of Classification Search ..... Plt./232
See application file for complete search history.

(56) References Cited

OTHER PUBLICATIONS

GTITM UPOVROM Citation for 'Gendipbic' as Per QZ PBR 20081468; Jun. 26, 2008.*

* cited by examiner

*Primary Examiner* — Kent L Bell
(74) *Attorney, Agent, or Firm* — Mark P. Bourgeois

(57) ABSTRACT

A new and distinct cultivar of *Mandevilla* plant named 'Gendipbic' that is characterized by pink flowers, dark green leaves, medium height and stems with anthocyanin coloration.

1 Drawing Sheet

Botanical classification: *Mandevilla sanderi.*
Variety denomination: 'Gendipbic'.

BACKGROUND OF THE INVENTION

The present invention relates to a new and distinct cultivar of *Mandevilla* plant botanically known as *Mandevilla sanderi* and hereinafter referred to by the cultivar name 'Gendipbic'.

The new cultivar is the product of a breeding program conducted by the inventor in a cultivated area of Hagenbach, Germany. The objective of the breeding program is to develop new *Mandevilla* cultivars that have large pink flowers.

'Gendipbic' originated from the crossing of the female or seed parent a proprietary selection of *Mandevilla sanderi* identified as 'DN 201' (not patented) and the male or pollen parent a proprietary selection of *Mandevilla sanderi* identified as 'DN 211' (not patented). The cultivar 'Gendipbic' was selected by the inventor in June of 2006 as a single plant within the progeny of the stated cross in a controlled environment of Hagenbach, Germany.

Asexual reproduction by terminal cuttings of the new cultivar 'Gendipbic' were first done in October of 2006 in Hagenbach, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Mandevilla* cultivar 'Gendipbic'. These traits in combination distinguish 'Gendipbic' as a new and distinct cultivar apart from other existing varieties of *Mandevilla* known to me.

1. *Mandevilla* 'Gendipbic' exhibits pink flowers.
2. *Mandevilla* 'Gendipbic' exhibits dark green leaves.
3. *Mandevilla* 'Gendipbic' exhibits a medium height.
4. *Mandevilla* 'Gendipbic' exhibits stems with anthocyanin coloration.

The closest comparison variety is *Mandevilla* 'Sunmandecripin' (U.S. Plant Pat. No. 15,539). 'Gendipbic' is different than 'Sunmandecripin' in having flowers that have a basal inner throat that is orange-red and a distal outer throat that is dark pink. 'Sunmandecripin' has a basal inner throat that is orange and a distal outer throat that is light pink.

The new cultivar 'Gendipbic' is distinguishable from the female parent *Mandevilla* 'DN 201' in having lighter red flowers with a smaller diameter corolla.

The new cultivar 'Gendipbic' is distinguishable from the male parent *Mandevilla* 'DN 211' in having lighter red flowers with a larger diameter corolla.

BRIEF DESCRIPTION OF THE DRAWING

The accompanying photograph illustrates the distinguishing traits of *Mandevilla* 'Gendipbic'. The plant in the photograph shows an overall view of an 8 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Mandevilla* cultivar named 'Gendipbic'. Data was collected in Hagenbach, Germany from 8 month old plants grown under glass greenhouse conditions. The plants were grown in 13 cm. diameter containers. The time of year was Summer and the daytime temperature ranged from 18 to 26° Centigrade. The temperature at night ranged from 16 to 20° Centigrade. The light level was 5 to 25 klux. No photoperiodic treatments or growth retardants were used. Color determinations are in accordance with The Royal Horticultural Society Colour Chart 2001 edition, except where general color terms of ordinary dictionary significance are used. The growing requirements are similar to the species.

'Gendipbic' has not been tested under all possible conditions and phenotypic differences may be observed with variations in environmental, climatic, and cultural conditions, however, without any variance in genotype.

Botanical classification: *Mandevilla sanderi* cultivar 'Gendipbic'.

Parentage: 'Gendipbic' resulted from the crossing of the following parent plants:

*Female parent*.—A proprietary selection of *Mandevilla sanderi* identified as 'DN 201'.

*Male parent*.—A proprietary selection of *Mandevilla sanderi* identified as 'DN 211'.

Vigor: Moderate.

Propagation: Terminal cuttings.

*Time to initiate roots* (*winter*).—Approximately 15 days to produce roots on an initial cutting.

*Time to initiate roots* (*summer*).—Approximately 10 days to produce roots on an initial cutting.

*Time to produce a rooted cutting or liner*.—8 weeks in Winter and 7 weeks in Summer.

*High temperature tolerance*.—38 degrees Centigrade.

*Low temperature tolerance*.—4 degrees Centigrade.

*Root system*.—Fibrous, fleshy.

Plant form: Perennial, upright and vining plant habit. Slightly woody plant base with herbaceous younger shoots. Initially upright. Can develop twines under low light conditions.

*Plant height*.—35 cm.

*Lateral branch dimensions*.—Length: About 30 cm. Diameter: About 3.0 mm.

*Internode length*.—4.3 cm.

*Strength*.—Medium strong.

*Texture*.—Smooth, glabrous, pubescence absent.

*Color*.—146 C.

*Anthocyanin coloration*.—59D.

Foliage:

*Arrangement*.—Decussate, simple.

*Length*.—6.8 cm.

*Width*.—5.2 cm.

*Shape*.—Broad obovoid.

*Apex*.—Acuminate.

*Base*.—Rounded to cordate.

*Margin*.—Entire.

*Texture*.—Upper and lower surfaces, smooth, glabrous, no pubescence.

*Venation pattern*.—Pinnate, reticulate.

*Color*.—Developing foliage, upper surface: 137B. Developing foliage, lower surface: 144A. Fully expanded foliage, upper surface: 135A; venation, 145D. Fully expanded foliage, lower surface: 147B to 147C; venation, 145D.

*Petiole length*.—1.9 cm.

*Petiole diameter*.—1.8 mm.

*Petiole texture*.—Smooth, glabrous, pubescence absent.

*Petiole color upper and lower surfaces*.—145D.

Inflorescence:

*Inflorescence type*.—Racemose, 2 to 4 single flowers per inflorescence.

*Inflorescence dimensions*.—9 cm. in diameter and 11 cm. in height.

*Flowering season*.—Summer to late autumn, flowering continuous during this period.

*Flower longevity*.—About 3 to 6 weeks.

*Fragrance*.—None.

*Flower shape*.—Flared trumpet, corolla fused, five-parted; petals imbricate; flowers roughly star-shaped.

*Flower dimensions*.—7.5 cm. in diameter and 7 cm. in depth.

*Bud shape*.—Obtrullate.

*Bud dimensions*.—8 cm. in length and 1.7 cm in diameter.

*Bud color*.—63A with a base 145C.

*Corolla shape*.—Tube and funnel shaped.

*Corolla diameter*.—7.5 cm.

*Tube dimensions*.—20 mm. in length and 3 mm. in diameter.

*Tube texture*.—Glabrous.

*Tube color*.—137A.

*Throat length*.—34 mm.

*Throat width distal end*.—20 mm.

*Throat texture*.—Glabrous.

*Throat color basal half outer side*.—154C.

*Throat color distal half outer side*.—54A.

*Throat color basal half inner side*.—31A.

*Throat color distal half inner side*.—58B.

*Limb shape*.—Spatulate with slight undulation and recurved distal end.

*Limb tip*.—Acuminate.

*Limb texture*.—Glabrous (both surfaces).

*Limb margin*.—Entire.

*Limb color*.—Inner side 58B, outer side 54A.

Peduncles:

*Dimensions*.—3.6 cm. in length and 2.5 mm. in diameter.

*Texture*.—Smooth, glabrous.

*Strength*.—Flexible, strong.

*Color*.—144A.

Pedicels:

*Dimensions*.—1.5 cm. in length and 2.0 mm. in diameter.

*Color*.—143C.

*Anthocyanin coloration*.—47B.

*Pubescence*.—Absent.

Calyx:

*Arrangement*.—5 sepals fused at the base.

*Sepal shape*.—Lanceolate.

*Sepal dimensions*.—6 mm. in length and 1.9 mm. in width.

*Sepal apex*.—Acute.

*Sepal margin*.—Entire.

*Sepal texture*.—Glabrous (both surfaces).

*Color basal half*.—147C (both surfaces).

*Color of distal half*.—147D with tips 45B (both surfaces).

Reproductive organs:

*Stamen number*.—5.

*Filament color*.—7B.

*Anther shape*.—Elliptic.

*Anther dimensions*.—9 mm. in length and 1.5 mm. in diameter.

*Anther color*.—155A.

*Amount of pollen*.—Scarce.

*Pollen color*.—11B.

*Ovary color*.—145D.

*Pistil quantity*.—One.

*Pistil length*.—About 2.4 cm.

*Stigma shape*.—Conical.

*Stigma color*.—145D.

*Style length*.—About 2.4 cm.

*Style color*.—145D.

Seed: Seed production has not been observed.

Disease and pest resistance: Plants of the new *Mandevilla* have not been observed for disease or pest resistance.

The invention claimed is:

1. A new and distinct variety of *Mandevilla* plant named 'Gendipbic' as described and illustrated.

* * * * *

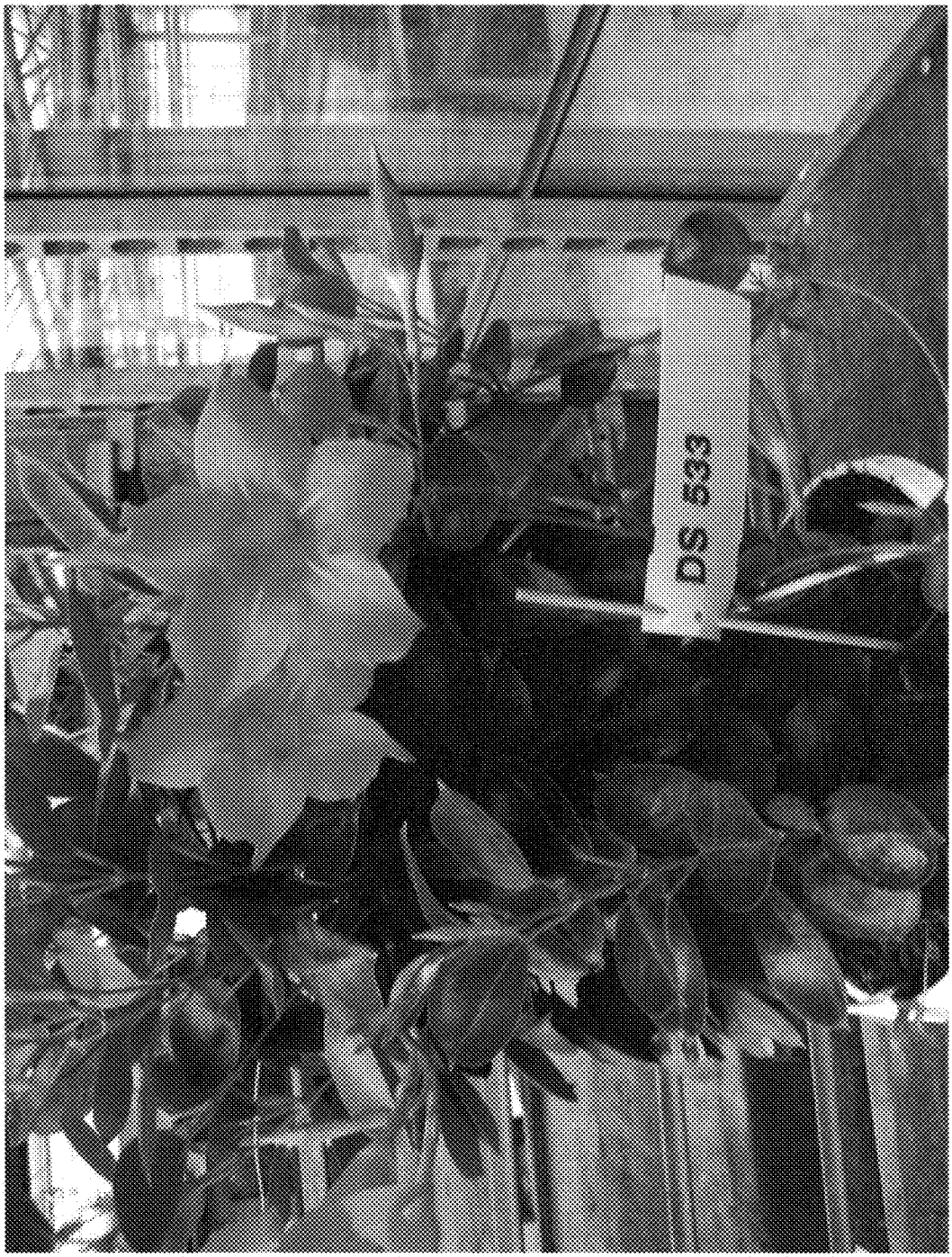
DS 633